(12) United States Patent
Fujita et al.

(10) Patent No.: US 7,569,599 B2
(45) Date of Patent: Aug. 4, 2009

(54) INTERMEDIATES FOR THE PRODUCTION OF OPTICALLY ACTIVE CYCLOPROPYLAMINE DERIVATIVES AND PROCESS FOR THE PRODUCTION OF THE INTERMEDIATES

(75) Inventors: Masao Fujita, Toyama (JP); Yutaka Kitagawa, Tokyo (JP); Makoto Muto, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 301 days.

(21) Appl. No.: 10/582,400

(22) PCT Filed: Sep. 30, 2004

(86) PCT No.: PCT/JP2004/014368

§ 371 (c)(1),
(2), (4) Date: Jun. 12, 2006

(87) PCT Pub. No.: WO2005/056526

PCT Pub. Date: Jun. 23, 2005

(65) Prior Publication Data

US 2007/0117988 A1    May 24, 2007

(30) Foreign Application Priority Data

Dec. 12, 2003    (JP) .............................. 2003-415398

(51) Int. Cl.
*A61K 31/40* (2006.01)
(52) U.S. Cl. ..................................................... 514/429
(58) Field of Classification Search .................. 514/429; 548/566

See application file for complete search history.

(56) References Cited

FOREIGN PATENT DOCUMENTS

| EP | 0 266 922 | 5/1988 |
|---|---|---|
| JP | 1-139577 | 6/1989 |
| JP | 8-277284 | 10/1996 |
| WO | WO 96/39407 | 12/1996 |
| WO | 00/56718 | 9/2000 |
| WO | 02/40478 | 5/2002 |
| WO | WO 2006/012443 | 2/2006 |

OTHER PUBLICATIONS

Kobayashi, Takashi et al., "Novel 2-Amino-1,4-dihydropyridine Calcium Antagonists. II. Synthesis and Antihypertensive Effects of 2-Amino-1, 4-dihydropyridine Derivatives Having N, N-Dialkylaminoalkoxycarbonyl Groups at 3-and/or 5-Position", Chem. Pharm. Bull., vol. 43, No. 5, pp. 797-817, 1995.
Inagaki, Hiroaki et al., "Synthesis and Structure-Activity Relationships of 5-Amino-6-fluoro-1-[(1R,2S)-2-fluorocyclopropan-1-yl]-8-methylquinolonecarboxylic Acid Antibacterials Having Fluorinated 7-[(3R)-3-(1-Aminocyclopropan-1-y1]pyrrolidin-1-yl] Substituents", J. Med. Chem., vol. 46, No. 6, pp. 1005-1015, 2003.
Christophe Laroche, et al., "Titanium-mediated synthesis of bicyclic cyclopropylamines from unsaturated nitriles", Tetrahedron Letters, vol. 44, 2003, pp. 2485-2487.
Philippe Bertus, et al., "Ti (II)-Mediated Conversion of a-Heterosubstituted (O, N, S) Nitriles to Functionalized Cyclopropylamines. Effect of Chelation on the Cyclopropanation Step", J. Org. Chem., vol. 67, 2002, pp. 3965-3968.
Philippe Bertus, et al., "Ti-Mediated Chemoselective Conversion of Cyanoesters and Cyanoamides into β-Aminoesters and 1-Azaspirolactams Bearing a Cyclopropane Ring", Letter, Synlett, No. 2, ISSN 0936-5214, 2003, pp. 265-267.
Stefan Wiedemann, et al., "Primary 1-Arylcyclopropylamines from Aryl Cyanides with Diethylzinc and Titanium Alkoxides†", Organic Letters, vol. 5, No. 5, 2003, pp. 753-755.

*Primary Examiner*—Rebecca L Anderson
*Assistant Examiner*—Shawquia Young
(74) *Attorney, Agent, or Firm*—Oblon, Spivak, McClelland, Maier & Neustadt, P.C.

(57) ABSTRACT

A process for producing an optically active compound represented by formula (4), or a salt thereof,

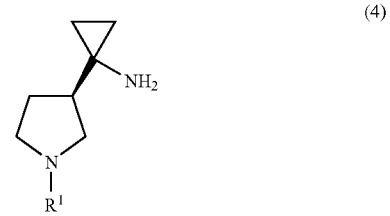

(4)

wherein $R^1$ represents a protecting group.

15 Claims, No Drawings

INTERMEDIATES FOR THE PRODUCTION OF OPTICALLY ACTIVE CYCLOPROPYLAMINE DERIVATIVES AND PROCESS FOR THE PRODUCTION OF THE INTERMEDIATES

TECHNICAL FIELD

The present invention relates to intermediates needed for production of an optically active cyclopropylamine derivative represented by the following formula (6):

[F1]

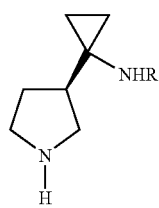

(6)

wherein R is a protecting group for the amino group, which is useful for the construction of a substituent on a quinolone compound. This invention also relates to a process for producing the intermediates.

BACKGROUND ART

Quinolone carboxylic acid derivatives are widely used as synthetic antibacterial agents in the medical field. Notwithstanding such usefulness, the derivatives are fraught with therapeutically serious problems due to growing emergence of resistant bacteria, such as MRSA. Even so, quinolone carboxylic acid derivatives exhibit not only excellent capability of killing MRSA but also antibacterial activity against resistant Gram-positive bacteria, thus serving as compounds able to solve various problems involved in resistant bacteria.

In production of a quinolone carboxylic acid derivative; e.g., the quinolone carboxylic acid derivatives shown below, an optically active compound represented by formula (6) is of great importance for the construction of a substituent present at the 7-position thereof (Patent Documents 1 and 2).

[F2]

(Patent Document 1)

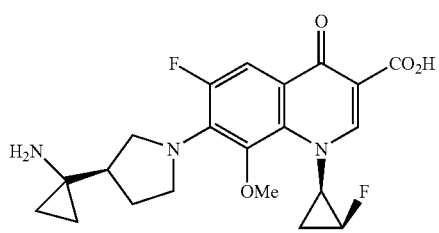

-continued (Patent Document 2)

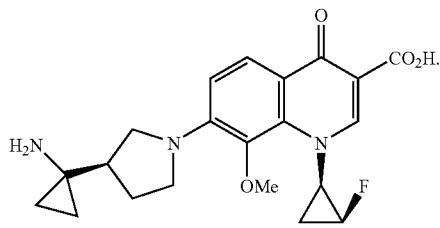

Thus far various methods have been known for producing an optically active compound represented by formula (6) (Patent Documents 1, 2, and 3).
[Patent Document 1] WO96/23782
[Patent Document 2] WO2002/40478
[Patent Document 3] WO96/39407

DISCLOSURE OF THE INVENTION

Problems to be Solved by the Invention

However, previous methods are required to take lengthy steps for production, and also need to be subjected either to the resolution through column chromatography or to the resolution through crystallization in order to obtain an optically active compound. Hence many problems remained to be solved from the viewpoint of industrial applications.

The objective of the present invention is to provide a process for producing intermediates needed for production of an optically active compound represented by formula (6), which enable the compound (6) to be readily synthesized through simple production steps without optical resolution, and also to provide such intermediate compounds used therein.

Means for Carrying Out the Invention

The present inventors have found that the optically active compound represented by formula (6) can be obtained without optical resolution, through the following simple process: a nitrile compound (3) is obtained from an easily available optically active pyrrolidinol (1) (described hereinbelow) via a compound (2); the nitrile compound (3) is reacted with a reagent which has been prepared from a titanium(IV) reagent and an alkylmetal compound, to thereby yield a compound (4); the substituent amino group of the compound (4) is protected with a protecting group R to thereby yield a compound (5); and the protecting group $R^1$ which has protected the ring amino group of the compound (5) is removed. The present invention was accomplished on this finding.

The present invention provides a process for producing an optically active compound represented by formula (4):

[F4]

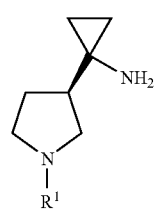

(4)

(wherein $R^1$ represents a protecting group of the amino group) or a salt thereof, characterized in that a reagent prepared from an titanium(IV) reagent and an alkylmetal compound is reacted with an optically active compound represented by formula (3):

[F3]

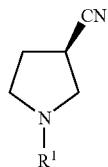

(3)

wherein $R^1$ has the same meaning as defined above, optionally in the presence of a Lewis acid.

The present invention also provides a compound represented by formula (1):

[F5]

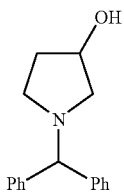

(1)

or an optically active species thereof; a compound represented by formula (2'):

[F6]

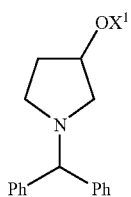

(2')

wherein $X^1$ represents a methanesulfonyl group or a p-toluenesulfonyl group, or an optically active species thereof; a compound represented by formula (3'):

[F7]

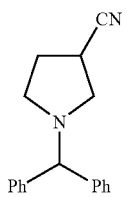

(3')

or an optically active species thereof.

The present invention also provides a compound represented by formula (4'):

[F8]

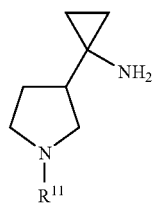

(4')

wherein $R^{11}$ represents a benzyl group, a phenethyl group, a benzyloxycarbonyl group, a methoxyphenyl group, a diphenylmethyl group or a trityl group, or an optically active species thereof, or a salt of the compound or the species; a compound represented by formula (5'):

[F9]

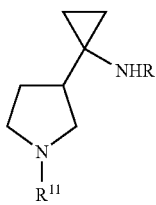

(5')

wherein $R^{11}$ represents a benzyl group, a phenethyl group, a benzyloxycarbonyl group, a methoxyphenyl group, a diphenylmethyl group or a trityl group, and R represents a protecting group of the amino group, or an optically active species thereof; and a compound represented by formula (7).

[F10]

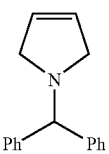

(7)

Effects of the Invention

According to the present invention, an optically active intermediate compound represented by formula (6), which is a useful raw material for producing quinolone derivatives which exhibit excellent antibacterial activity against, for example MRSA, can readily be synthesized through a simple process without optical resolution.

BEST MODE FOR CARRYING OUT THE INVENTION

The intermediate compounds of the present invention are produced through the following reaction scheme:

[F11]

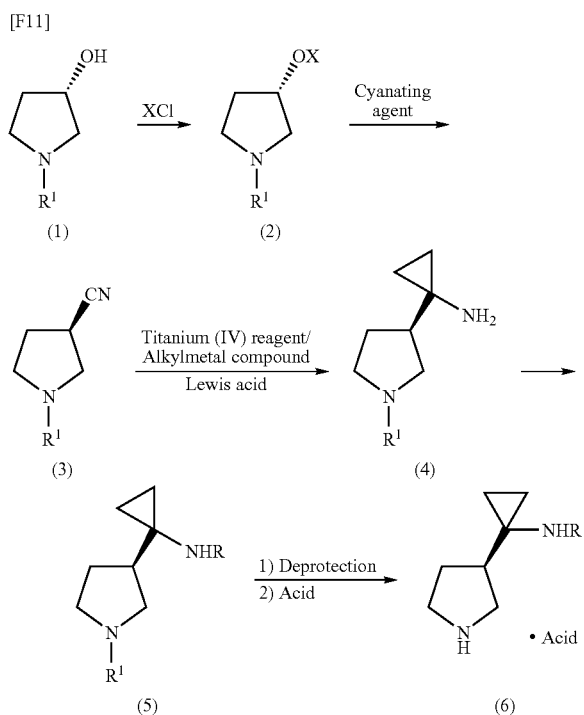

wherein R and $R^1$ represent protecting groups of the amino groups, and X represents an alkylsulfonyl group or an arylsulfonyl group.

Specifically, a compound (2) obtained from an optically active pyrrolidinol (1) is converted into a stereochemically inverted optically active nitrile compound (3), and the nitrile compound (3) is reacted with a reagent prepared from a titanium(IV) reagent and an alkylmetal compound, optionally in the presence of a Lewis acid, to thereby produce an optically active compound (4) having the maintained stereostructure as the compound (3). The substituent amino group of the optically active compound (4) is protected by a protecting group R, to thereby produce a compound (5).

The optically active compound represented by formula (6) can be produced through removal of the protecting group $R^1$ for the ring amino group.

The compound (1) is readily synthesized through condensation of (3S)-hydroxypyrrolidine and an aldehyde compound or a ketone compound and subsequent reduction of the condensed product. The reaction may proceed in the presence of a Lewis acid. Alternatively, the compound (1) may be produced through reaction of (3S)-3-hydroxypyrrolidine with an alkyl halide (the alkyl group may be substituted by an aryl group) or with an acylation agent (e.g., acid chloride, acid anhydride). No particular limitation is imposed on the solvent employed in the reaction, so long as the solvent does not adversely affect the reaction.

Alternatively, the compound (1) may be obtained selectively through a known asymmetric hydroboration of an N-substituted-3-pyrroline compound (J. Org. Chem., 47, 5074 (1982); J. Org. Chem., 51, 4296 (1986); JP-A-2003-040863; JP-A-2003-286255). Of N-substituted-3-pyrroline compounds, 1-diphenylmethyl-3-pyrroline is particularly useful in industrial-scale production- since 1-diphenylmethyl-3-pyrroline can be crystallized and purified with isopropyl ether. The N-substituted-3-pyrroline compound may be obtained through reaction of cis-1,4-dichloro-2-butene with an alkylamine or an aralkylamine.

Examples of the protecting group $R^1$ for the amino group include alkoxycarbonyl groups such as tert-butoxycarbonyl, methoxycarbonyl, ethoxycarbonyl, and 2,2,2-trichlorocarbonyl; aralkyloxycarbonyl groups such as benzyloxycarbonyl, paramethoxybenzyloxycarbonyl, and paranitrobenzyloxycarbonyl; acyl groups such as formyl, acetyl, propanoyl, tert-butyloyl, pivaloyl, benzoyl; aralkyl groups such as benzyl, α-methylbenzyl, trityl, diphenylmethyl(benzhydryl), paranitrobenzyl, paramethoxybenzyl, and phenethyl; methoxyphenyl; and alkoxycarbonylamino groups such as tert-butoxycarbonylamino. The protecting group is preferably benzyl, phenethyl, benzyloxycarbonyl, methoxyphenyl, diphenylmethyl, trityl, or a similar group, particularly preferably diphenylmethyl.

The compound (1) is preferably 1-diphenylmethyl-3-hydroxypyrrolidine, particularly preferably (3S)-1- diphenylmethyl-3-hydroxypyrrolidine.

The compound (2) may be obtained through reaction of the compound (1) with an alkylsulfonyl chloride which may have a substituent or with an arylsulfonyl chloride which may have a substituent in the presence of a base through a ordinary method. Examples of the alkylsulfonyl chloride include methanesulfonyl chloride and trifluoromethanesulfonyl chloride. Examples of the arylsulfonyl chloride include phenylsulfonyl chloride and p-toluenesulfonyl chloride.

The compound (2) is in a crystalline compound and thus is of great industrial usefulness, since a purification process through column chromatography as described in JP-A-1989-143852 can be eliminated. The compound (2) is preferably 1-diphenylmethyl-3-mesyloxypyrrolidine or 1-diphenylmethyl-3-tosyloxypyrrolidine, particularly preferably (3S)-1-diphenylmethyl-3-mesyloxypyrrolidine or (3S)-1-diphenylmethyl-3-tosyloxypyrrolidine.

The compound (3) may be produced through reaction of the compound (2) with a cyanating agent. Examples of the cyanating agent include sodium cyanide, potassium cyanide, and tetrabutylammonium cyanide. No particular limitation is imposed on the reaction solvent, so long as the reaction solvent does not adversely affect the reaction.

The reaction involves complete inversion of the stereostructure. Therefore, the compound (3) has a stereostructure which is completely inverted from that of the compound (2).

The protecting group $R^1$ in the compound (3) is preferably benzyl, phenethyl, benzyloxycarbonyl, methoxyphenyl, diphenylmethyl, trityl, or a similar group, particularly preferably diphenylmethyl. 3-Cyano-1-(1,1-diphenylmethyl)pyrrolidine is a crystalline compound and thus is of great industrial usefulness, since its purification is readily performed.

The compound (4) is obtained through reaction of the compound (3) with a titanium(IV) reagent and an alkylmetal compound. The reaction may be performed in the presence of a Lewis acid.

The amounts of the titanium(IV) reagent and the alkylmetal compound employed will next be described. The amount of the titanium(IV) reagent employed is 1 to 5 times, preferably 1 to 3 times in mole that of the compound (3). The amount of an ethyl Grignard reagent is 2 to 20 times, preferably 2 to 5 times in mole that of the compound (3). When a Lewis acid is added, the amount of the Lewis acid employed is 0.5 to 5 times, preferably 1 to 3 times in mole that of the compound (3).

The titanium reagent is preferably a titanium(IV) alkoxide. Titanium(IV) tetraalkoxides or substituted titanium(IV) trialkoxides may be employed. For example, titanium(IV) tetraisopropoxide, methyltitanium(IV) triisopropoxide, chlorotitanium(IV) triisopropoxide, or a similar substance may be employed. Of these, a titanium(IV) tetraalkoxide is preferred, with titanium(IV) tetraisopropoxide being particularly preferred.

The alkylmetal compound may be a Grignard reagent or a dialkylzinc compound. The alkylmetal compound is preferably an ethylmetal compound, such as an ethyl Grignard reagent or diethylzinc. The alkylmetal compound is preferably an alkyl Grignard reagent such as an ethyl Grignard reagent.

The ethyl Grignard reagent may be ethylmagnesium chloride or ethylmagnesium bromide, and these reagent may be dissolved in diethylether, tetrahydrofuran, or a similar solvent. The ethyl Grignard reagent is preferably ethylmagnesium bromide.

The dialkylzinc compound is preferably diethylzinc, which may be employed in solution. The dialkylzinc compound may be dissolved in ether, tetrahydrofuran, or a similar solvent.

Examples of the Lewis acid include trifluoroboron-ether complex (e.g., trifluoroboron-diethyl ether complex), trifluoroboron-tetrahydrofuran complex, halogenated metal (e.g., aluminum chloride), and alkali metal salts (e.g., lithium iodide), with trifluoroboron-ether complex being preferred.

Examples of the solvent employed in the reaction for production of the compound (4) from the compound (3) include ether compounds (e.g., tetrahydrofuran, diethylether, dioxane, and dimethoxyethane), aromatic compounds (e.g., benzene, toluene, and xylene), and chloride compounds (e.g., methylene chloride and chloroform), with ether solvents being particularly preferred.

The reaction temperature is −30 to 170° C., preferably 0 to 110° C. The compound (3), the titanium(IV) reagent, and the ethyl Grignard reagent may be reacted for 30 minute to 3 hours. The Lewis acid may be added to the compound (3), titanium(IV) reagent, and ethyl Grignard reagent before reaction, or after the three are caused to react for 30 minutes to 3 hours.

The reaction is performed under an atmosphere of inert gas such as nitrogen gas or argon gas. The compound (3), the titanium(IV) reagent, and the ethyl Grignard reagent may be mixed together simultaneously, or the compound (3) may be added after the titanium(IV) reagent and the ethyl Grignard reagent are mixed. Together with the Lewis acid, an alkoxide such as sodium ethoxide or sodium isopropoxide may be added.

In the thus-produced compound (4), the stereostructure of the starting material compound (3) is maintained.

The protecting group $R^1$ in the compound (4) is preferably benzyl, phenethyl, benzyloxycarbonyl, methoxyphenyl, diphenylmethyl, or trityl.

The compound (4) is preferably 3-(1-aminocyclopropyl)-1-(1,1-diphenylmethyl)pyrrolidine, particularly preferably (3R)-3-(1-aminocyclopropyl)-1-(1,1-diphenylmethyl)pyrrolidine.

Examples of the salt of the compound (4) include inorganic acid salts (e.g., hydrochloride, sulfate, and nitrate) and organic acid salts such as carboxylates (e.g., oxalate, tartrate, and mandelate).

The compound (5) is synthesized through protection of the substituent amino group of the compound (4). Examples of the protecting group R for said amino group include alkoxycarbonyl groups such as tert-butoxycarbonyl, methoxycarbonyl, ethoxycarbonyl, and 2,2,2-trichlorocarbonyl; aralkyloxycarbonyl groups such as benzyloxycarbonyl, paramethoxybenzyloxycarbonyl, and paranitrobenzyloxycarbonyl; acyl groups such as formyl, acetyl, propanoyl, tert-butyloyl, pivaloyl, and benzoyl; aralkyl groups such as benzyl, α-methylbenzyl, trityl, diphenylmethyl(benzhydryl), paranitrobenzyl, paramethoxybenzyl, and phenethyl; methoxyphenyl; and alkoxycarbonylamino groups such as tert-butoxycarbonylamino. The protecting group R is preferably alkoxycarbonyl or acyl.

The optically active compound represented by formula (6) is produced through removal of the protecting group $R^1$ for the substituent amino group of the compound (5).

The deprotection reaction may be performed through the method described in JP-A-2002-322148, which may be appropriately modified depending on the type of the protecting group. The protecting group forming an ester may be removed through hydrolysis in the presence of a base such as sodium hydroxide, sodium carbonate, or sodium hydrogencarbonate. When the protecting group forming an ester is benzyloxycarbonyl or a similar group, hydrolysis may be performed under reducing conditions.

Preferably, the thus-produced optically active cyclopropylamine derivative (6) is converted into a salt with an inorganic acid (e.g., hydrochloric acid, sulfuric acid, or nitric acid) or an organic acid such as carboxylic acid (e.g., optically inactive oxalic acid, tartaric acid, or mandelic acid), since such a salt is readily purified to give a highly optically pure product. The salt is particularly preferably oxalate or hydrochloride.

EXAMPLES

The present invention will next be described in more detail by way of examples, which should not be construed as limiting the invention thereto.

Example 1

(3S)-1-Diphenylmethyl-3-hydroxypyrrolidine

Benzophenone (5.47 g) was dissolved in tetrahydrofuran under an argon atmosphere. Titanium(IV) tetraisopropoxide (13.3 mL) was added to the solution at room temperature. After 0.25 h, (3S)-3-hydroxypyrrolidine (2.61 g) in tetrahydrofuran (5.5 mL) was added dropwise to the mixture, and the resultant mixture was stirred at room temperature for 1 hour. After 1 h, polymethylhydrosiloxane (5.8 mL) was added to the reaction mixture, and the resultant mixture was stirred. After 19 h, a 28 wt. % aqueous sodium hydroxide solution (60 mL) was added to the reaction mixture, and the resultant mixture was refluxed for 0.5 hour. The temperature of the reaction mixture was lowered to room temperature and then extracted with toluene. The formed aqueous layer was again extracted with toluene, and the organic layers were combined together, washed with saturated brine, and then dried over sodium sulfate. The drying agent was removed through filtration, and the filtrate was concentrated under reduced pressure, to thereby yield crystalline residue. The residue was subjected to silica gel chromatography, to thereby give the target compound (4.65 g, yield 61.2%). The target compound was purified through recrystallization from isopropyl alcohol.

$^1$H-NMR (400MHz, CDCl$_3$) δ: 1.72-1.78 (1H, m), 2.12-2.26 (2H, m), 2.44 (1H, dd, J=5.0, 10.4 Hz), 2.62-2.64 (1H, m), 2.76-2.81 (1H, m), 4.21 (1H, s), 4.31 (1H, s), 7.14-7.45 (10H, m)

Example 2

(3S)-1-Diphenylmethyl-3-mesyloxypyrrolidine (3S)-1-Diphenylmethyl-3-hydroxypyrrolidine (1.10 g) was dissolved in methylene chloride (11 mL). Triethylamine (1.1 mL) was added dropwise to the solution, and the resultant mixture was stirred under cooling with ice.

Methanesulfonyl chloride (0.5 mL) was added dropwise to the reaction mixture, and the temperature of the resultant mixture was raised to room temperature. After 3 h, saturated sodium hydrogencarbonate (13 mL) was added dropwise to the mixture, and the resultant mixture was extracted with methylene chloride. The formed aqueous layer was again extracted with methylene chloride, and the methylene chloride layers were combined together and then washed with saturated brine.

Whole was dried over sodium sulfate. The drying agent was removed through filtration, and the filtrate was concentrated under reduced pressure, to thereby give the target compound (1.52 g, quantitative amount).

$^1$H-NMR (400MHz, CDCl$_3$) δ: 2.04-2.12 (1H, m), 2.25-2.34 (1H, m), 2.37-2.43 (1H, m), 2.66-2.72 (1H, m), 2.75-2.83 (2H, m), 2.96 (3H, s), 4.24 (1H, s), 5.15-5.19 (1H, m), 7.16-7.45 (10H, m)

Example 3

(3R)-3-Cyano-1-benzylpyrrolidine (3S)-1-Benzyl-3-mesyloxypyrrolidine (2.56 g) was dissolved in acetonitrile (3.6 mL). Tetrabutylammonium cyanide (4.95 g) was added to the solution, and the mixture was stirred at 65° C. for 6.5 hours. Saturated sodium hydrogencarbonate (13 mL) and toluene were added dropwise to the reaction mixture, whereby the organic layer was extracted. The organic layer was washed with water and then dried over sodium sulfate. The drying agent was removed through filtration, and the filtrate was concentrated under reduced pressure. The residue was subjected to silica gel chromatography, to thereby give the target compound (1.42 g, yield 76.2%) as a pale yellow oil.

Example 4

(3R)-3-Cyano-1-(1,1-diphenylmethyl)pyrrolidine (3S)-1-Diphenylmethyl-3-mesyloxypyrrolidine (1.25 g) was dissolved in acetonitrile (1.75 mL). Tetrabutylammonium cyanide (1.87 g) was added to the solution, and the mixture was stirred at 65° C. for 12 hours. Saturated sodium hydrogencarbonate (7 mL) and toluene were added dropwise to the reaction mixture, whereby the organic layer was extracted. The organic layer was washed with water and then dried over sodium sulfate. The drying agent was removed through filtration, and the filtrate was concentrated under reduced pressure, to thereby yield crystals. The residue was subjected to silica gel chromatography, to thereby give the target compound (0.766 g, yield 77.4%) as colorless crystals.

$^1$H-NMR (400 MHz, CDCl$_3$) δ: 2.07-2.25 (2H, m), 2.50-2.63 (2H, m), 2.68-2.78 (2H, m), 2.97-3.02 (1H, m), 4.25 (1H, s), 7.17-7.45 (10H, m)

Example 5

(3R)-3-(1-aminocyclopropyl)-1-(1,1-diphenylmethyl)pyrrolidine (3R)-3-Cyano-1-(1,1-diphenylmethyl)pyrrolidine (0.70 g) was dissolved in tetrahydrofuran under an argon atmosphere. Titanium(IV) tetraisopropoxide (0.86 mL) and ethylmagnesium bromide (1.78 mL, 3 mol/L ether solution) were added to the solution at room temperature. After 05 h, trifluoroboron-diethyl ether complex (0.67 mL) was added dropwise to the mixture, and the resultant mixture was stirred at room temperature. After 18 h, 2 mol/L aqueous sodium hydroxide (30 mL) was added to the reaction mixture, and the resultant mixture was stirred for 0.25 hours. The product that precipitated was collected through filtration and then extracted. The formed aqueous layer was again extracted with ethyl acetate, and the organic layers were combined together, washed with saturated brine, and dried over sodium sulfate. The drying agent was removed through filtration, and the filtrate was concentrated under reduced pressure, to thereby yield crystals. The residue was subjected to silica gel chromatography, to thereby give the target compound (0.374 g, yield 48%).

$^1$H-NMR (400 MHz, CDCl$_3$) δ: 0.36-0.52 (4H, m), 1.56-1.68 (3H, m), 1.90-1.95 (2H, m), 2.35-2.49 (2H, m), 2.50-2.56 (2H, m), 4.13 (1H, s), 7.15-7.45 (10H, m)

Example 6

(3R)-3-[1-(tert-Butoxycarbonylamino)cyclopropyl]-1-(1,1-diphenylmethyl)pyrrolidine (3R)-3-(1-Aminocyclopropyl)-1-(1,1-diphenylmethyl)pyrrolidine (0.34 g) was dissolved in tert-butyl alcohol (1.7 mL), and 1 mol/L aqueous sodium hydroxide (3.0 mL) was added to the solution, followed by stirring. Di-tert-butyl dicarbonate (0.40 mL) was added to the mixture, and the resultant mixture was stirred at room temperature for 7 hours. The reaction mixture was extracted with chloroform. The formed aqueous layer was again extracted with chloroform, and the organic layers were combined together, washed with saturated brine, and dried over sodium sulfate. The drying agent was removed through filtration, and the filtrate was concentrated under reduced pressure, to thereby yield crystalline. The residue was subjected to silica gel chromatography, to thereby give the target compound (0.336 g, yield 74%) as pale yellow crystals.

$^1$H-NMR (400 MHz, CDCl$_3$) δ: 0.63-0.89 (4H, m), 1.44 (9H, s), 1.59-1.65 (1H, m), 1.82-1.96 (1H, m), 2.19-2.60 (5H, m), 4.14 (1H, m), 5.19 (1H, s), 7.14-7.45 (10H, m)

Example 7

(3R)-3-(1-Aminocyclopropyl)-1-benzylpyrrolidine (3R)-3-Cyano-1-benzylpyrrolidine (1.40 g) was dissolved in tetrahydrofuran (21.0 mL) under an argon atmosphere. Titanium(IV) tetraisopropoxide (2.40 mL) and ethylmagnesium bromide (5.00 mL, 3 mol/L solution in ether) were added to the solution at room temperature. After 0.5 h, trifluoroboron-diethyl ether complex (1.90 mL) was added dropwise to the mixture, and the resultant mixture was stirred at room temperature. After 4 h, 2 mol/L aqueous sodium hydroxide (30 mL) was added to the reaction mixture, followed by stirring for 0.25 hours. The product that precipitated was collected through filtration and then extracted. The formed aqueous layer was again extracted with ethyl acetate, and the organic layers were combined together, washed with saturated brine, and dried over sodium sulfate. The drying agent was removed through filtration, and the filtrate was concentrated under reduced pressure, to thereby the target compound as a crude product (1.65 g).

$^1$H-NMR (400 MHz, CDCl$_3$) δ: 0.35-0.55 (4H, m), 1.62-1.69 (3H, m), 1.90-1.96 (2H, m), 2.39 (1H, dd, J=6.0, 9.2 Hz), 2.56-2.59 (2H, m), 2.63 (1H, dd, J=7.6, 9.2 Hz), 3.59 (2H, abq, J=12.8, 23.2 Hz), 7.23-7.33 (5H, m)

Example 8

(3R)-3-[1-(tert-Butoxycarbonylamino)cyclopropyl]-1-benzylpyrrolidine

Crude (3R)-3-(1-aminocyclopropyl)-1-benzylpyrrolidine (1.65 g) was dissolved in tert-butyl alcohol (8.3 mL), and 1 mol/L aqueous sodium hydroxide (15.0 mL) was added to the solution, followed by stirring. Di-tert-butyl dicarbonate (2.60 mL) was added to the reaction mixture, and the resultant mixture was stirred at room temperature for 12 hours. The reaction mixture was extracted with ethyl acetate. The formed aqueous layer was again extracted with ethyl acetate, and the organic layers were combined together, washed with saturated brine, and dried over sodium sulfate. The drying agent was removed through filtration, and the filtrate was concentrated under reduced pressure, to thereby yield crystalline. The residue was subjected to silica gel chromatography, to thereby give the target compound (0.675 g, yield 28%) as a yellow oil.

$^1$H-NMR (400 MHz, CDCl$_3$) δ: 0.65-0.87 (4H, m), 1.44 (9H, s), 1.53-1.68 (1H, m), 1.84-1.95 (1H, m), 2.24-2.33 (2H, m), 2.45-2.51 (1H, m), 2.54-2.67 (1H, m), 2.68-2.79 (1H, m), 3.58 (2H, s), 5.06 (1H, brs), 7.24-7.32 (5H, m)

Example 9

(3R)-3-[1-(tert-Butoxycarbonylamino)cyclopropyl] pyrrolidine monooxalate

Removal of Benzyl Group (3R)-3-[1-(tert-Butoxycarbonylamino)cyclopropyl]-1-benzylpyrrolidine (2.90 g, 9.16 mmol) was dissolved in ethanol (29.0 mL), and 5% palladium carbon was added to the solution in an equiamount of the pyrrolidine. Under a hydrogen atmosphere (atmospheric pressure), the mixture was stirred at 50° C. for 4 hours (see JP-A-2002-322148). After the starting material had been consumed, the mixture was left to cool and then filtered. The filtrate was concentrated under reduced pressure. Isopropyl alcohol (4.4 mL) was added to the residue, and the mixture was cooled with ice. Oxalic acid dihydrate (825 mg, 9.16 mmol) was added to the mixture, and isopropyl ether (29.0 mL) was added thereto, followed by stirring for 1 hour. The crystals that precipitated were collected through filtration and then dried under reduced pressure, to thereby give the target compound (2.18 g, yield 75.2%).

Removal of Diphenylmethyl Group (3R)-3-[1-(tert-Butoxycarbonylamino)cyclopropyl]-1-(1,1-diphenylmethyl)pyrrolidine (250 mg, 0.64 mmol) was dissolved in ethanol (2.50 mL), and 5% palladium carbon was added to the solution in an equiamount of the pyrrolidine. Under a hydrogen atmosphere (atmospheric pressure), the mixture was stirred at 50° C. for 3 hours (see JP-A-2002-322148). After the starting materials had been consumed, the reaction mixture was left to cool and then filtered. The filtrate was concentrated under reduced pressure. Isopropyl alcohol (0.38 mL) was added to the residue, and the mixture was cooled with ice. Oxalic acid dihydrate (57.6 mg, 0.64 mmol) was added to the mixture, and isopropyl ether (2.50 mL) was added thereto, followed by stirring for 1 hour. The crystals that precipitated were collected through filtration and then dried under reduced pressure, to thereby give the target compound (163.5 mg, yield 80.8%).

$^1$H-NMR (400 MHz, d$_6$-DMSO) δ: 0.64 (4H, s), 1.36 (9H, s), 1.57-1.68 (1H, m), 1.82-1.92 (1H, m), 2.81-2.86 (1H, m), 3.01-3.08 (1H, m), 3.15-3.24 (2H, m)

Example 10

(3S)-1-Diphenylmethyl-3-hydroxypyrrolidine (3S)-3-Hydroxypyrrolidine (2.0 g) was dissolved in acetonitrile (10.0 mL) under cooling with ice. Triethylamine (4.8 mL) was added to the solution, and bromodiphenylmethane (5.7 g) in acetonitrile (10.0 mL) was added dropwise to the mixture, followed by stirring at room temperature for 4.5 hours. After completion of reaction, the insoluble material was removed through filtration, and water and toluene were added to the filtrate, whereby the organic layer was extracted. The formed aqueous layer was again extracted with toluene, and the organic layers were combined together, washed with saturated brine, and dried over sodium sulfate. The drying agent was removed through filtration, and the filtrate was concentrated under reduced pressure, to thereby yield crystalline residue. The residue was subjected to silica gel chromatography, to thereby give the target compound (5.2 g, yield 89.7%). The thus-obtained compound can be crystallized through treatment with hexane-ethyl acetate, alcohol-water, and so on.

Example 11

(3S)-1-Diphenylmethyl-3-tosyloxypyrrolidine (3S)-1-Diphenylmethyl-3-hydroxypyrrolidine (4.00 g) was dissolved in methylene chloride (11 mL), and the solution was stirred under cooling with ice. Triethylamine (3.3 mL) was added dropwise to the reaction mixture, and p-toluenesulfonyl chloride (3.61 g) was added to the resultant mixture, followed by stirring at room temperature for 12 hours and then at 40° C. for 4.5 hours. Since the starting materials partially remained unconsumed, triethylamine (1.1 mL) and p-toluenesulfonyl chloride (1.5 g) were added to the reaction mixture and then stirred for 24 hours. The reaction mixture was extracted with water and chloroform, and the organic layer was dried over sodium sulfate. The drying agent was removed through filtration, and the filtrate was concentrated under reduced pressure, to thereby yield crystalline residue. The residue was subjected to silica gel chromatography, to thereby give the target compound (4.40 g, yield 68.5%). The thus-obtained compound was purified through recrystallization from isopropyl alcohol.

H-NMR (400 MHz, CDCl$_3$) δ: 1.93-1.99 (1H, m), 2.09-2.14 (1H, m), 2.29-2.35 (1H, m), 2.41 (3H, s), 2.60-2.64 (3H, m), 4.17 (1H, s), 4.95-4.98 (1H, m), 7.13-7.40 (12H, m), 7.75 (2H, J=7.6 Hz, d).

Referential Example 1

1-Diphenylmethyl-3-pyrroline cis-1,4-Dichloro-2-butene (15.4 g) was dissolved in methanol (100.0 mL). Aminodiphenylmethane (18.3 g), sodium acetate (16.4 g), and potassium iodide (1.0 g) were added to the solution, and the mixture was stirred at 65° C. for 6.5 hours. The reaction mixture was extracted with methylene chloride and 1 mol/L aqueous sodium hydroxide, and the organic layer was dried over sodium sulfate. The drying agent was removed through filtration, and the filtrate was concentrated under reduced pressure. Isopropyl ether was added to the residue, and the mixture was heated. The insoluble material was removed through filtration, and the filtrate was concentrated. The formed crystals were collected through filtration. The crystals were further washed with a small amount of isopropyl ether, to thereby give the target compound (11.62 g, yield 41%) as white crystals.

$^1$H-NMR (400 MHz, CDCl$_3$) δ: 3.38 (4H, s), 4.57 (1H, s), 5.79 (2H, s), 7.15 (2H, J=7.6 Hz, t), 7.27 (4H, J=7.6 Hz, t), 7.49 (4H, J=7.6 Hz, d)

Example 12

(3S)-1-Diphenylmethyl-3-hydroxypyrrolidine

Sodium borohydride (0.235 mg) was suspended in tetrahydrofuran (2.0 mL) in an argon flow, and the suspension was cooled with ice. Optically active α-pinene (0.63 mL) and boron trifluoride-ether complex (0.25 mL) were added dropwise to the suspension, and the mixture was stirred for 12 hours. 1-Diphenylmethyl-3-pyrroline (0.24 g) was added to the reaction mixture, and the resultant mixture was allowed to react for 9 hours. Thereafter, 30% aqueous hydrogen peroxide (2 mL) and 6 mol/L aqueous sodium hydroxide (2 mL) were added dropwise to the reaction mixture. After 3 h, the reaction mixture was extracted with methylene chloride, and the formed organic layer was dried over sodium sulfate. The drying agent was removed through filtration, and the filtrate was concentrated under reduced pressure, to thereby yield crystalline residue. The residue was subjected to silica gel chromatography, to thereby give the target compound (0.200 g, yield 79%). HPLC analysis (through use of a Daicel Chiral Pack AD-RH) of the thus-obtained compound indicates that the compound has an optical purity of 72% ee.

The invention claimed is:

1. A process for producing an optically active compound represented by formula (4), or a salt thereof,

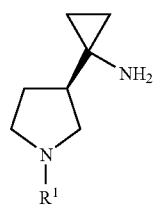

wherein $R^1$ represents a protecting group, the process comprising:

reacting a compound of formula (1)

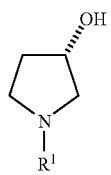

with an alkylsulfonyl chloride or an arylsulfonyl chloride, in the presence of a base, to form a compound of formula (2)

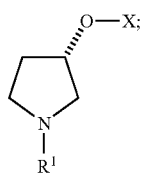

wherein X represents an alkylsulfonyl group or an arylsulfonyl group,

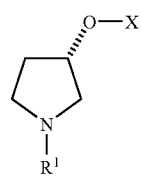

reacting the compound of formula (2) with a cyanating agent to form a compound of formula (3)

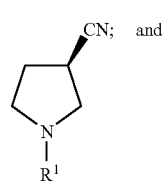

reacting the compound of formula (3) with an alkyl metal compound, a titanium (IV) reagent, and optionally a Lewis acid, to form the compound of formula (4), or a salt thereof.

2. The process according to claim 1, wherein the titanium (IV) reagent is a titanium(IV) alkoxide.

3. The process according to claim 1, wherein the titanium (IV) reagent is titanium(IV) tetraisopropoxide, methyltitanium(IV) triisopropoxide, or chlorotitanium(IV) triisopropoxide.

4. The process according to any one of claims 1 to 3, wherein the alkylmetal compound is an ethylmetal compound.

5. The process according to any one of claims 1 to 3, wherein the alkylmetal compound is an alkyl Grignard reagent or a dialkylzinc.

6. The process according to claim 5, wherein the alkyl Grignard reagent is an ethyl Grignard reagent.

7. The process according to claim 6, wherein the ethyl Grignard reagent is ethylmagnesium chloride or ethylmagnesium bromide.

8. The process according to claim 7, wherein the ethyl Grignard reagent is ethylmagnesium bromide.

9. The process according to any one of claims 1 to 3, wherein the alkylmetal compound is diethylzinc.

10. The process of claim 1, comprising reacting the compound of formula (3) with an alkyl metal compound, a titanium (IV) reagent, and a Lewis acid, to form the compound of formula (4), or a salt thereof.

11. The process of claim 1,
wherein the alkylsulfonyl chloride is selected from the group consisting of methanesulfonyl chloride and trifluoromethanesulfonyl chloride;
wherein the arylsulfonyl chloride is selected from the group consisting of phenylsulfonyl chloride and p-toluenesulfonyl chloride;
wherein the cyanating agent is selected from the group consisting of sodium cyanide, potassium cyanide, and tetrabutylammonium cyanide;

wherein the titanium (IV) reagent is selected from the group consisting of titanium (IV) tetraisopropoxide, methyltitanium (IV) triisopropoxide, and chlorotitanium (IV) triisopropoxide;

wherein the Lewis acid is selected from the group consisting of trifluoroboron, aluminum chloride, and lithium iodide;

wherein the alkyl metal compound is selected from the group consisting of ethyl magnesium chloride, ethyl magnesium bromide, and diethyl zinc; and wherein the protecting group is selected from the group consisting of tert-butoxycarbonyl, methoxycarbonyl, ethoxycarbonyl, 2,2,2-trichlorocarbonyl, benzyloxycarbonyl, paramethoxybenzyloxycarbonyl, paranitrobenzyloxycarbonyl, formyl, acetyl, propanoyl, tert-butyloyl, pivaloyl, benzoyl, benzyl, α-methylbenzyl, trityl, diphenylmethyl(benzhydryl), paranitrobenzyl, paramethoxybenzyl, phenethyl, methoxyphenyl, and tert-butoxycarbonylamino.

12. The process of claim 11, wherein the base is triethylamine.

13. The process of claim 11, wherein the compound of formula (3) is reacted with the alkyl metal compound the titanium (IV) reagant and the Lewis acid.

14. The process of claim 11, wherein the compound of formula (1) is reacted with the arylsulfonyl chloride.

15. The process of claim 11, wherein the compound of formula (1) is reacted with the alkylsulfonyl chloride.

* * * * *